United States Patent
Yamada

[11] Patent Number: 5,881,410
[45] Date of Patent: Mar. 16, 1999

[54] AIR MAT FOR OPERATION BED

[75] Inventor: Masaaki Yamada, Kanagawa, Japan

[73] Assignee: Teikoku Hormone MFG. Co., Ltd., Tokyo, Japan

[21] Appl. No.: 727,570

[22] PCT Filed: Apr. 26, 1995

[86] PCT No.: PCT/JP95/00828

§ 371 Date: Oct. 23, 1996

§ 102(e) Date: Oct. 23, 1996

[87] PCT Pub. No.: WO95/29660

PCT Pub. Date: Nov. 9, 1995

[30] Foreign Application Priority Data

Apr. 28, 1994 [JP] Japan .................... 6-111695

[51] Int. Cl.$^6$ .................................................. A47C 27/10
[52] U.S. Cl. ........................................ 5/713; 5/421; 5/284
[58] Field of Search ................................ 5/713, 714, 421, 5/422, 284

[56] References Cited

U.S. PATENT DOCUMENTS

| | | | |
|---|---|---|---|
| 2,998,817 | 9/1961 | Armstrong | 5/422 |
| 4,149,066 | 4/1979 | Niibe . | |
| 4,175,297 | 11/1979 | Robbins et al. . | |
| 4,652,726 | 3/1987 | Femino et al. | 219/217 |
| 4,814,583 | 3/1989 | Rainey | 219/494 |
| 5,267,365 | 12/1993 | Walter . | |
| 5,402,542 | 4/1995 | Viard | 5/421 |
| 5,509,154 | 4/1996 | Shafer et al. | 5/453 |

FOREIGN PATENT DOCUMENTS

| | | |
|---|---|---|
| 57-57836 | 9/1955 | Japan . |
| 60-129918 | 8/1985 | Japan . |
| 3-502410 | 6/1991 | Japan . |

*Primary Examiner*—Kenneth J. Dorner
*Assistant Examiner*—Frederick Conley
*Attorney, Agent, or Firm*—Nixon & Vanderhye

[57] ABSTRACT

A plane heater is mounted on the lower surface of an air mat having a function of preventing bedsore, and the temperature of a patient is maintained via an air layer of the air mat. A time delay caused by heating via the air layer is adjusted through prediction control.

12 Claims, 14 Drawing Sheets

WITHOUT AIR MAT

WITH AIR MAT

WITH HEATER A

WITH HEATER B

AIR MAT FOR OPERATION BED

FIELD OF THE INVENTION

The present invention relates to an air mat, and more particularly to an air mat for an operation bed.

BACKGROUND OF THE INVENTION

The lower surface of a human body lying on a bed receives the force of gravity of the upper part of the human body. Circulating system organs such as blood vessels and lymphatic vessels are pressed and their functions are degraded. A healthy person can turn on the bed to change the bodily area pressed by the force of gravity and maintain normal functions of the circulating system.

However, elderly persons forced to always lie on bed or patients applied with an anesthetic cannot turn on the bed with their own forces, and the same lying posture on beds is forced to be maintained. As a person lies on a bed for a long time with the same posture, the lower part of the body on the bed is pressed by the gravitational force and the circulation system function is degraded so that the body has bedsore. In order to prevent bedsore, it is necessary to prevent a pressure (bodily pressure) from being applied to the body at the same area.

An air mat has been developed which can prevent bedsore. This air mat is constituted by a plurality group of air cells and compressed air is selectively introduced into each air cell group. If the compressed air is intermittently supplied, the surface area of a human body on the air mat is released from the bodily pressure during the period while the compressed air is not supplied so that the functions of circulating system organs can be recovered.

For example, an air mat on which a person Lies is constituted by a number of air cells, and the air cells are divided into two groups to which compressed air is alternately supplied. In this manner, even if a person lies on the air mat at the same posture, the area receiving the bodily pressure changes. Since the area receiving the bodily pressure changes, bedsore can be prevented.

With such an air mat, nursing work for a person, who cannot move the body with own force such as an always lying elderly person, can be reduced considerably.

In a surgical operation, the patient under operation is applied with an anesthetic or the like and cannot change the posture with own force. For a doctor performing an operation, it is necessary to maintain the same posture of the patient. In order to prevent bedsore of the patient under operation, an air mat capable of changing the area supporting the patient weight is very effective.

During an operation, a doctor moves his or her body and the temperature of the doctor rises. If the temperature of the operation room is high, the doctor sweats and there is a danger that the sweat drops on the affected part of the patient. From this reason, the temperature of an operation room is generally cooled to about 22° to 25° C.

A patient under operation maintains the same posture during the operation. In many cases, the patient is applied with an anesthetic so that the metabolism lowers. If a patient is left in the cooled room for a long time, the temperature of the patient lowers. The patient who lowers the temperature during an operation reduces the physical strength. As the physical strength of the patient under operation reduces, the recovery of the physical strength after the operation is hindered.

It is therefore desired to maintain the temperature of a patient under operation at a predetermined level.

Japanese Patent Laid-open Publication No. 60-129918 discloses an air mat having code heaters disposed at connection sections between adjacent air cells. Each air cell is made of a rubber or synthetic resin sheet and disposed adjacent, to other air cells to form the bed surface. There is a gap between adjacent cells and the code heater is disposed in this gap.

However, if the air mat having this structure is used as the air mat for an operation bed, the following problems occur. The patient under operation maintains a constant body posture during the operation. For convenience of a doctor performing an operation, an air mat for an operation bed cannot be made thick. If local heating is performed by a code heater, it is not easy to uniformly heat the patient body. A temperature distribution is likely to be generated on the body surface of the patient. It is therefore desired to perform uniform heating.

A bodily temperature recovery apparatus has also been developed which covers the body of a patient after the operation and blows heated air therein in order to recover the patient temperature lowered during the operation.

DISCLOSURE OF THE INVENTION

It is an object of the present invention to provide an air mat for an operation bed capable of preventing lowering a bodily temperature of a patient under operation without generating bedsore.

It is another object of the present invention to provide an air mat for an operation bed capable of preventing bedsore of a patient under operation and preventing lowering a bodily temperature.

According to one aspect of the present invention, there is provided an air mat equipment for an operation bed, comprising: a plurality group of air cells disposed along a bed surface extending in a longitudinal direction, each air cell being made of a deformable bag-shaped sheet and having an opening through which air passes, and the air cells being capable of cooperatively forming an elastic support surface at the upper surface thereof for placing a patient under operation; a plane heater of a sheet shape disposed under the plurality group of air cells and having an area covering a main portion of the patient body; a deformable bag for packing the plane heater and the plurality group of air cells; a temperature sensor disposed on the upper surface of the bag for generating a temperature signal representative of a detected temperature T; selective air supply means for selectively supplying air to the plurality group of air cells and being capable of sequentially changing a group of air cells not supplied with air; and control means responsive to the temperature signal for supplying a power to the plane heater in accordance with the detected temperature.

According to another aspect of the present invention, there is provided a method of driving an air mat for an operation bed capable of periodically changing a support area of the weight of a patient, comprising the steps of: activating and heating a heater provided on a lower surface of an air layer of the air mat; measuring a temperature $T_i$ with a sensor provided on an upper surface of the air layer of the air mat; comparing the measured temperature $T_i$ with a comparison temperature $(T_0 - \Delta T_1)$ lower than a target temperature To by $\Delta T_1$; and reducing drive current of the heater when the measured temperature $T_i$ reaches the comparison temperature $(T_0 - \Delta T_1)$.

The heater is of a plane sheet shape covering the main portion of a patient. Therefore, a uniform plane heating is possible. The main portion of a patient means an area including at least the torso of the upper body of a patient. The heater is disposed under the air layer and heat is conducted via the air layer to the upper patient. It is therefore possible to maintain the patient temperature more uniformly. There is a time delay between a temperature change in the heater and the temperature change in the upper surface of the air layer. However, the temperature at the upper surface of the air layer is measured to perform prediction control. High precision temperature control is therefore possible.

MOST PREFERRED EMBODIMENTS FOR PRACTICING THE INVENTION

An operation requires to maintain a constant body posture of a patient, and there is a possibility that bedsore is generated or the bodily temperature is lowered during a long time operation of three hours or longer. If the whole body is applied with an anesthetic, the patient cannot move the body with own will. If the body of the patient moves, the operation work of the doctor is hindered.

Therefore, the body posture of the patient under operation is maintained constant. If the patient lies for a long time at the constant posture, the lower part of the patient receiving the body weight degrades its circulating system and bedsore is generated. In order to prevent bedsore, an air mat is used.

The air mat is constituted by a plurality of air cells which include air cells with air inflated and air cells with the air pressure being released, and only the air cells with air inflated support the weight of a patient. By alternately changing the air cells with the air pressure being released, the bodily pressure can be dispersed. In this manner, the air cells for supporting the weight of a patient are periodically changed to prevent bedsore.

The temperature of an operation room is maintained about 22° to 25° C., for example, about 23° C., during the operation to prevent sweat of the doctor. The patient under operation is left in the low temperature with the metabolism being lowered for a long time. Therefore, the temperature of the patient under operation lowers and shivering or the like occurs after the operation because of the lowered bodily temperature.

In order to properly recover the physical strength of a patient after the operation, it is preferable to maintain the temperature of the patient under operation at a proper temperature. As a means for maintaining the bodily temperature of a patient, an electric sheet or an electric blanket may be used.

FIGS. 14A to 14E illustrate preliminary experiments for prevention of bedsore and maintenance of bodily temperature.

Figure 14A:
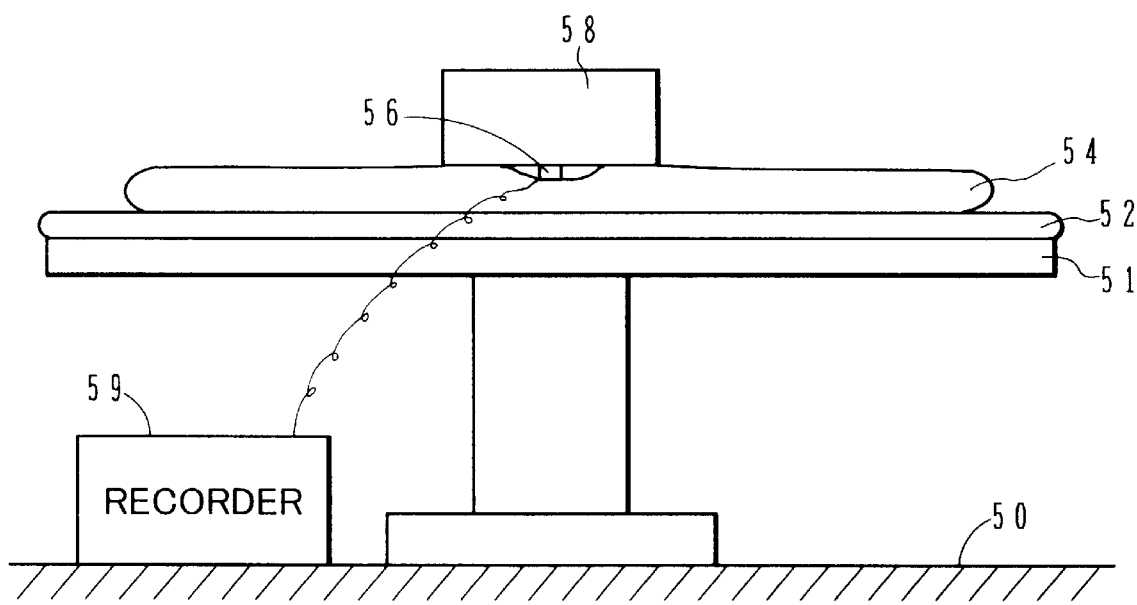
FIGS. 14A to 14E are a schematic side view and graphs illustrating preliminary experiments upon which the present invention is based.

FIG. 14A shows an apparatus used for the experiments. An operation bed 51 is placed on a floor 50, and a usual mat 52 is placed on the operation bed. The measuring apparatus has a pressure sensitive element 56 and a weight 58 placed thereon. The pressure sensitive element has a diameter of 9 mm, and the weight 58 is 12 Kg. The operation bed 51 has generally a width of about 45 to 50 cm, and a length of about 190 to 192 cm.

Figure 14B:
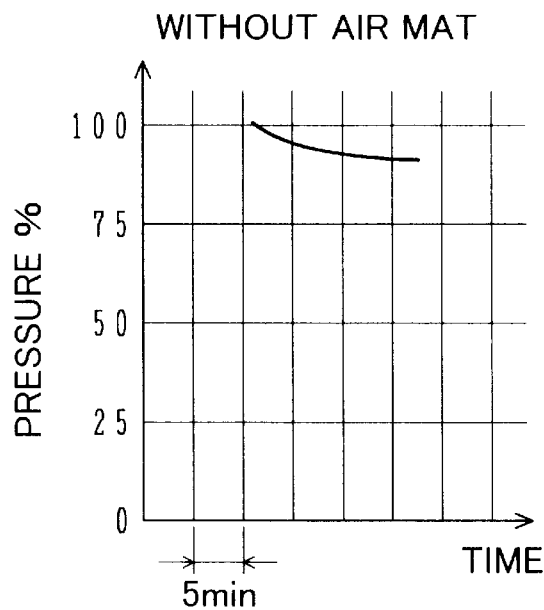

FIG. 14B shows the measurement results wherein the pressure sensitive element 56 and weight 58 are placed directly on the mat 52. The abscissa represents a lapse time, and the ordinate represents a normalized pressure received by the pressure sensitive element. If the pressure sensitive element 56 and weight 58 arc placed directly on the air mat 52, the pressure applied by the weight 58 reduces slightly with a time lapse, becomes about 93% after the lapse of 15 minutes, and thereafter hardly changes. If the constant bodily pressure is continuously received, the body of a patient will have bedsore.

In view of this, the air mat 54 is placed on the mat 52 and the bodily pressure is dispersed by alternately activating two groups of air cells in the air mat.

Figure 14C:
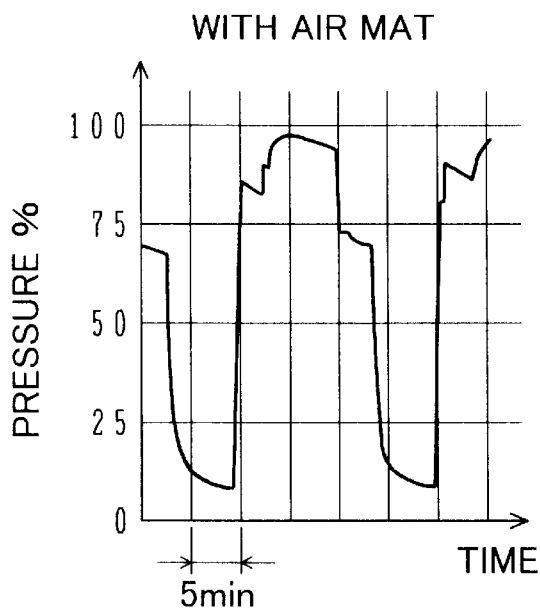

FIG. 14C shows the measurement results wherein the pressure sensitive element 56 is placed on the air mat 54 and the weight 58 is placed on the pressure sensitive element 56. While air is inflated into the air cells under the pressure sensitive element 56, the pressure by the weight 58 is applied to the pressure sensitive element 56, whereas as the air pressure in the air cells under the pressure sensitive element 56 is released, the pressure applied to the pressure sensitive element lowers considerably.

In the measurement results shown in the drawing, the pressure while an air pressure is applied to the air cells is about 98%, and the pressure applied to the pressure sensitive element 56 while the pressure is released lowers to about 8%. In this case, as the bodily pressure is released, the functions of the circulating system will be recovered and prevention of bedsore will be effective.

Similar experiments were conducted by placing a sheet heat insulating member on the mat 54 in order to maintain the temperature of a patient under operation.

Figure 14D:
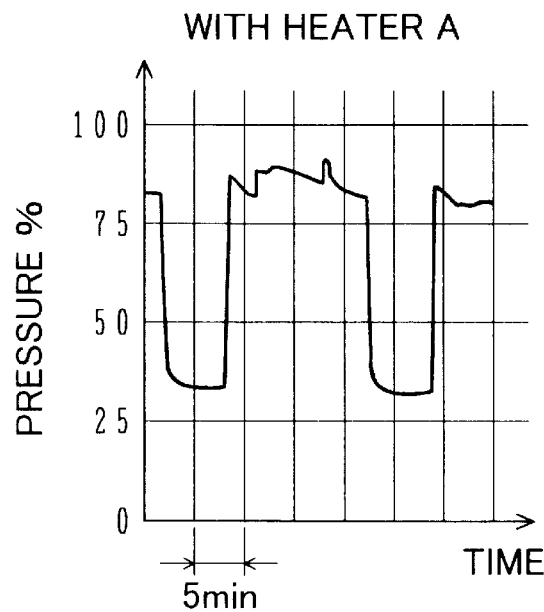
Figure 14E:
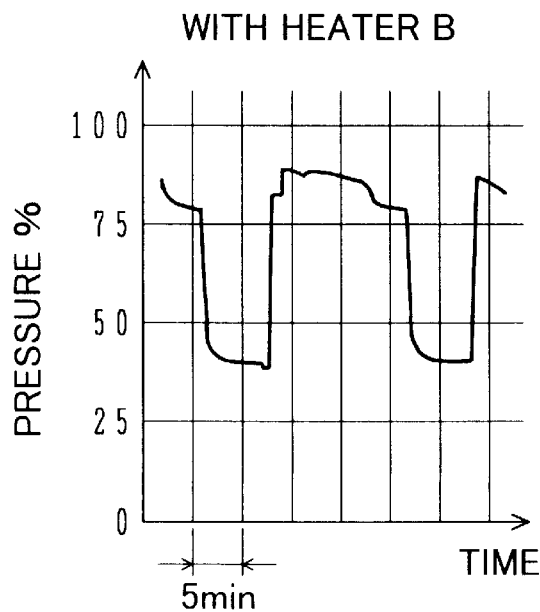

FIGS. 14D and 14E show experiment results wherein two types of heat insulating sheets are placed on the air mat 54 and the pressure sensitive element 56 and weight 58 are placed on the heat insulating sheet. While air is filled in the air cells under the pressure sensitive element and the pressure by the weight 58 is received by those air cells, the pressures in both the cases is about 90%. However, even if air in the air cells is deflated and the Load is released, the load of about 30 to 40% is left. Namely, if the heater sheet for maintaining the bodily temperature is placed on the air mat 54, the load releasing effect by the air mat is reduced considerably.

Basing upon the above experiment results, the present inventor has developed an air mat for an operation bed capable of maintaining the temperature of a patient without losing the load dispersing effect of the air mat.

Figure 1:
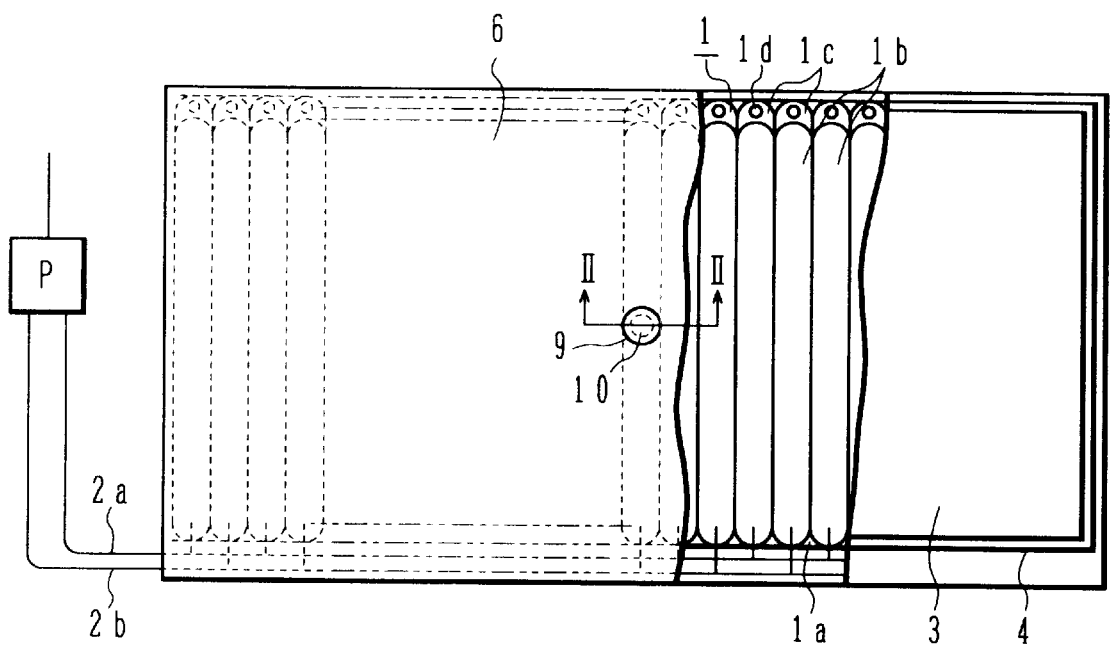
FIG. 1 is a partially broken plan view of an air mat according to an embodiment of the invention.
Figure 2:
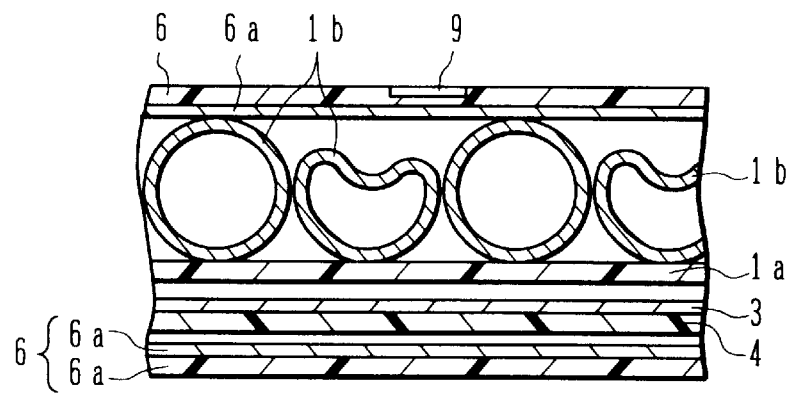
FIG. 2 is a cross sectional view taken along line II—II of FIG. 1.

FIGS. 1 to 5 are schematic diagrams showing the structure of an air mat according to an embodiment of the invention. FIG. 1 is a partially broken plan view of an air mat, and FIG. 2 is a cross sectional view taken along line II—II of FIG. 1. The air mat 1 includes a number of juxtaposed air cells 1b extending in the bed width direction. Each air cell 1b is made of an elongated bag of synthetic resin such as vinyl chloride, one end being closed and the other end being opened.

The closed end portion extends to form a support piece 1c. The opened ends of air cells are alternately connected to air supply pipes 2a and 2b. A support sheet 1a made of synthetic resin such as vinyl chloride and polypropylene is disposed under the air cells 1b. The support sheet 1a and air cells 1b are coupled by engaging means 1d such as a hook disposed at the closed end portion.

The two air supply pipes 2a and 2b extend from a pump P disposed outside of the bed to the side of the opened ends of the air cells 1b, and are alternately coupled to the air cells 1b. Specifically, the same air pressure source is connected to every second air cells 1b. While the first group of air cells 1b is supplied with compressed air, the air pressure in the second group of air cells 1b is released and then compressed air is supplied also to the second group of air cells. After the second group of air cells is sufficiently pressured, the pressure in the first group of air cells is released.

Next, while the second group of air cells 1b is maintained in a pressured state, compressed air is supplied to the first group of air cells whose air pressure having been released. After the first group of air cells is sufficiently pressured, the pressure in the second group of air cells is released. In this manner, the load area can be periodically changed while maintaining the body posture of a patient constant.

In order to hinder the operation work of a doctor while maintaining the body posture of a patient constant, it is preferable that the diameter of each air cell under the pressured state is about 4 to 8 cm. It is preferable that the diameter of each air cell is made smaller particularly at the bed central area which supports the main portion of a patient body. For example, the diameter of each air cell at the bed central area is set to about 5 cm, and that of each air cell at the bed opposite areas is set to about 6.5 cm. A ratio of the smaller cell diameter to the large cell diameter is preferably about 1.25 to 1.35.

In order to maintain the temperature of a patient, a heater is disposed adjacent to the lower side of the air mat 1. In order to heat uniformly, a plane heater is used which heats the whole surface on the side where the heater is disposed. As shown in FIG. 2, on the upper surface of the polypropylene sheet 4 excellent in insulation, heat resistance, and heat insulation, a carbon heater layer 3 containing carbon and silver is formed. An air mat 5 with a heating function is constituted by the air cells 1b, support sheet 1a, carbon heater layer 3, and support sheet 4. This air mat 5 with the heating function is housed in a bag 6. The bag 6 has a layer 6a formed on the inner surface of a synthetic resin sheet 6b made of polyester or the like excellent in heat resistance, heat insulation, and water proof, the layer 6a being made of infrared reflection material such as aluminum.

Figure 3:
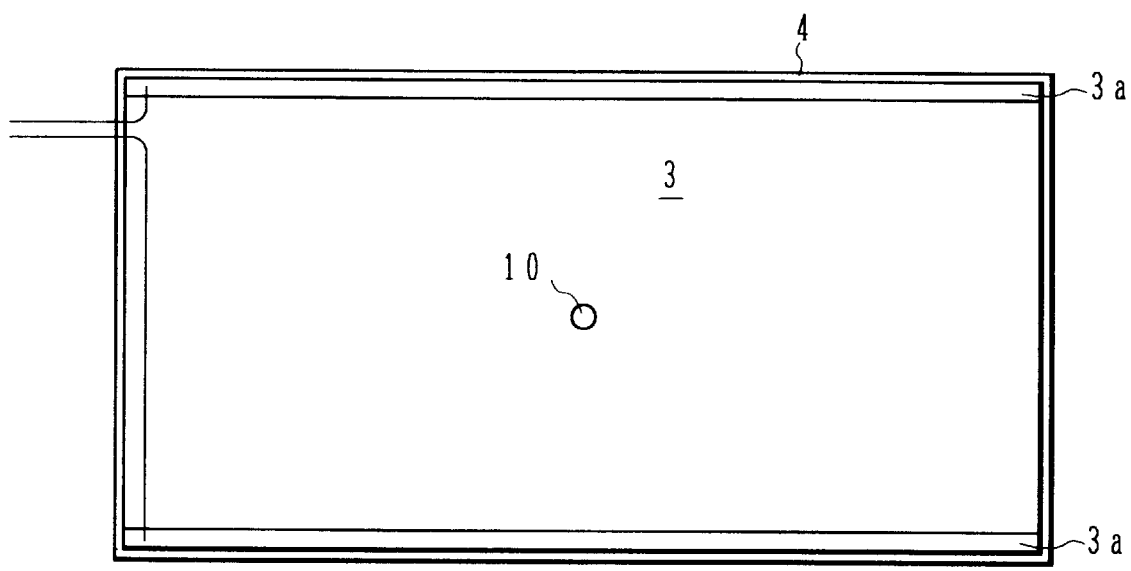
FIG. 3 is a plan view of the heater portion of the air mat.

As shown in FIG. 3, the carbon heater layer 3 is formed on generally the whole surface of the support sheet 4. Generally the whole surface means that the peripheral area is left as an idle area for use during manufacture processes. Therefore, the carbon heater layer 3 can heat generally uniformly a broad area of the bed area including the area which supports the body of a patient. A temperature detecting element 10 such as a thermistor is disposed at the central area of the upper surface of the carbon heater layer 3. This temperature detecting element 10 detects a temperature of the carbon heater layer 3 itself.

As shown in FIG. 3, the carbon heater layer 3 has electrodes 3a along the longer sides thereof so that current flows in parallel with the shorter sides.

A thin temperature detecting element 9 of high precision such as a semiconductor temperature sensor is buried in the upper portion of the bag 6. This temperature detecting element 9 detects a synthesized temperature of a temperature of a body lying thereon and a temperature of an air layer disposed thereunder.

Figure 4:
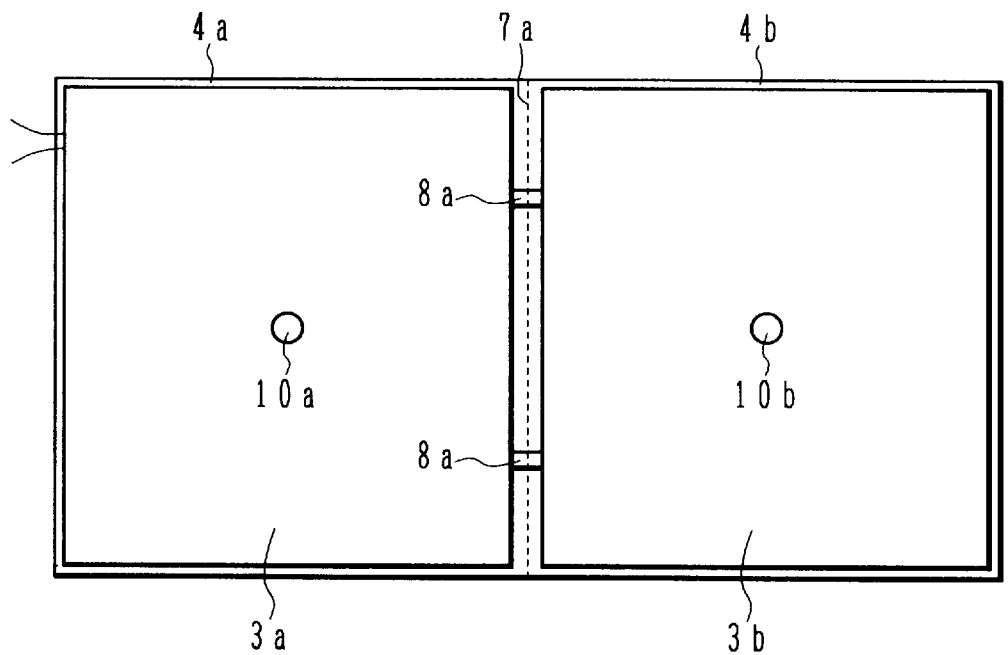
FIG. 4 is a plan view showing the layout of a heater portion over the whole air mat and heater temperature detecting sensors.

As shown in FIG. 4, two plane heaters may be formed over the whole bed area. The support sheet 4 is formed with a folding line 7a so that the support sheet 4 can be folded into two parts 4a and 4b in the longitudinal direction. On the surface of each part 4a, 4b of the support sheet, a carbon heater layer 3a, 3b described above is formed. One carbon heater layer 3a can heat an area of the upper half body of a patient including at least the torso, and both the carbon heater layers 3a and 3b can heat an area of a patient including generally all the body. These carbon heater layers 3a and 3b are electrically connected by flexible conductors durable to bending. At the central area of each carbon layer 3a, 3b, a temperature detecting element 10a, 10b such as a thermistor is disposed.

Figure 5:
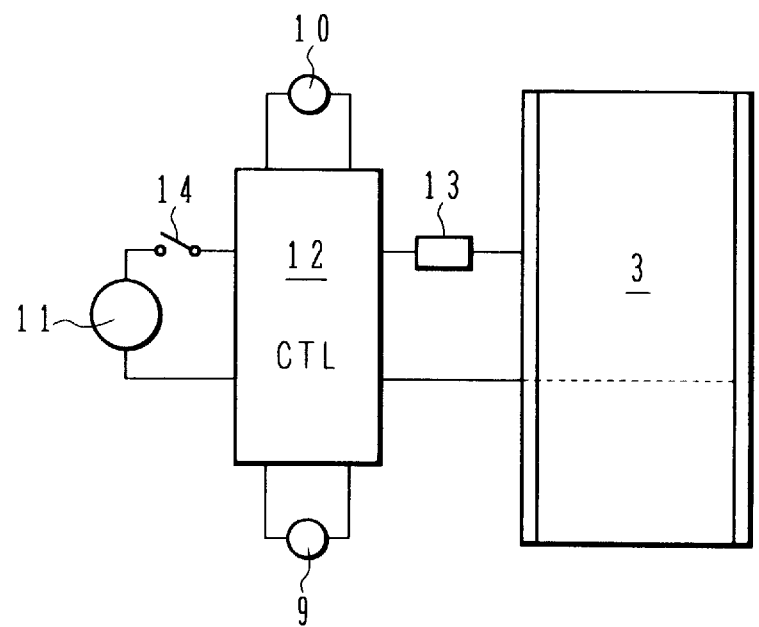
FIG. 5 is a block diagram of a heater control circuit of the air mat.

FIG. 5 is a schematic electronic circuit of the bed with the heater. A power source 11 is connected via a switch 14 to a control circuit 12. The control circuit 12 is connected via a fuse 13 to the plane heater 3. The fuse is a temperature fuse which is broken when an abnormal temperature is generated. Also connected to the control circuit 12 are a heater temperature detecting element 10 and a synthesized temperature detecting sensor 9 for detecting a synthesized temperature of a bodily temperature and a temperature of the air layer. The control circuit 12 compares a setting temperature with the synthesized temperature to control a drive power for the plane heater.

In the structure shown in FIG. 5, a control circuit may be provided for each heater 3a, 3b shown in FIG. 4, or a single control circuit may be provided for both the heaters 3a and 3b. The heaters 3a and 3b may be connected in parallel or serially. A single heater may be constituted without dividing it into a plurality of heaters. The heater may be divided into three or more parts.

Next, the operation of the air mat described above will be described. As the air pump P shown in FIG. 1 is driven, the air mat 1 is swelled into a usable state. In the circuit shown in FIG. 5, when the switch 14 is turned on, the control circuit 12 operates to turn on the plane heater 3, synthesized temperature detecting sensor 9, and heater temperature detecting sensor 10. The plane heater 3 generates heat and heats the air mat to a predetermined temperature. When the synthesized temperature detecting sensor 9 on the surface of the bag 6 detects the setting temperature, the drive current for the plane heater 3 is turned off. As the synthesized temperature lowers, current again flows through the plane heater 3 to perform a temperature raising operation. in this manner, the heating operation is repeated while the synthesized temperature is detected so that the temperature of a person lying on the bag 6 is heated to a predetermined temperature.

If the heater temperature sensor 10 detects a predetermined temperature or higher during heating the heater 3, it is considered as abnormal heating and the drive current for the heater 3 is turned off. if the heater temperature becomes the predetermined temperature or lower, the drive current for the plane heater 3 may be turned on again. If an abnormal temperature rise is detected, an operator checks the cause of the abnormal temperature rise, and the drive current is adapted not to be flowed unless the power source is reset after the cause is solved.

The setting temperature can be selected in the range from 35° to 42° C. If the temperature at the area in contact with the human body rises to 39° C. or higher, there is a danger that the patient has a low temperature burn. In order to prevent the low temperature burn, it is preferable to dispose a plurality of synthesized temperature detecting sensors at the main expected areas of the human body to control the synthesized temperature to 39° C. or lower.

Figure 6:
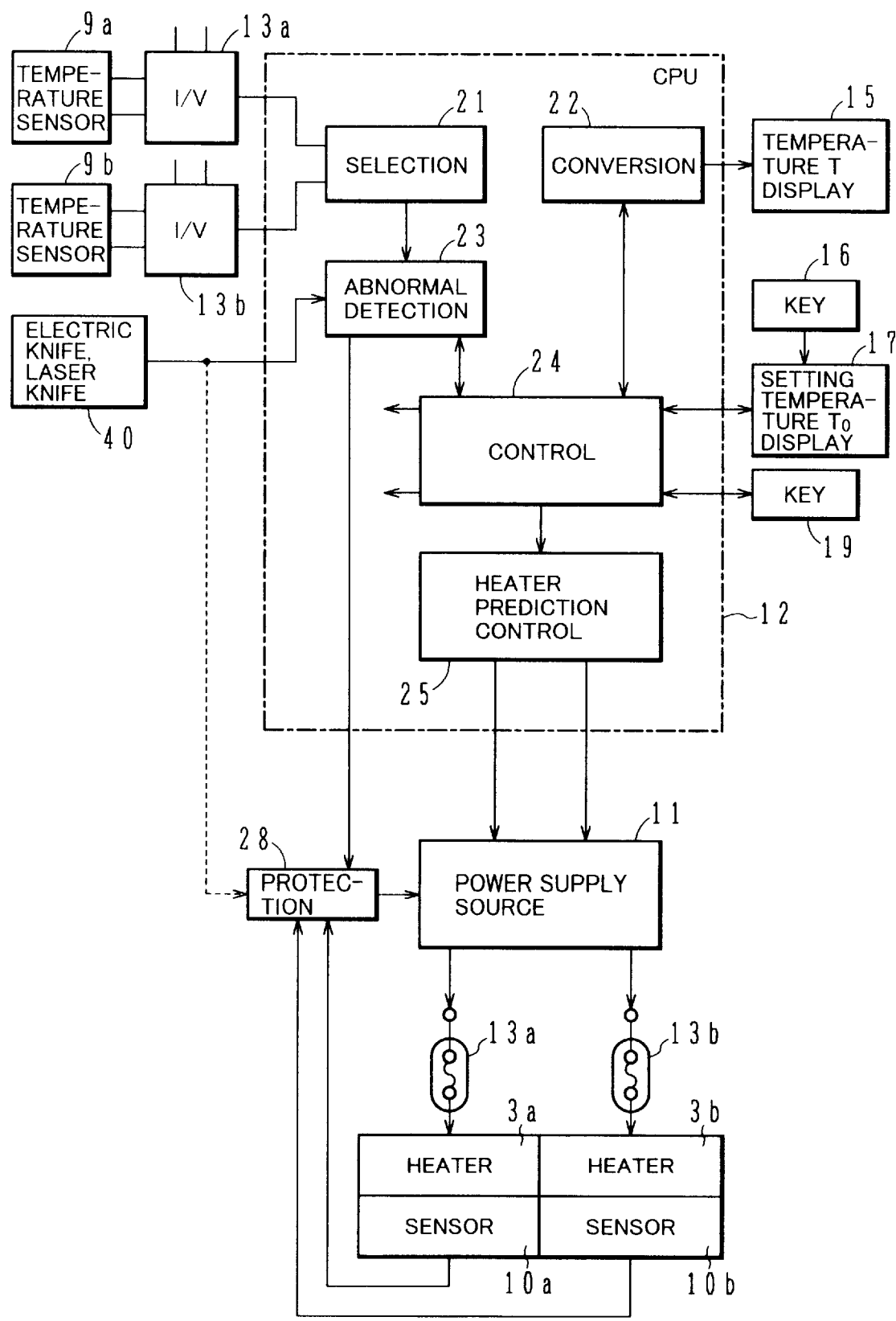
FIG. 6 is a block diagram showing the details of the heater control circuit of the air mat.

FIG. 6 is a block diagram showing the details of the control circuit. The two plane heaters 3a and 3b are disposed over the bed surface and are provided with temperature detecting sensors 10a and 10b. The plane heater can be heated, for example, to about 70° C. The temperature detecting sensors are provided for detecting a temperature much higher than this heater temperature. Drive current for the plane heaters 3a and 3b is supplied from a current supply source 11 via temperature fuses 13a and 13b. The temperature fuse 13 is broken when the plane heater 3 becomes an abnormally high temperature, and intercepts the drive current.

The current supply source 11 can selectively supply power to the plane heaters 3a and 3b, or can supply the drive current to the plane heaters 3a and 3b at the same time. The operation of the current supply source 11 is controlled by the control circuit 12.

A usable voltage is limited in many cases in an operation room in order to prevent noises from entering a cardiogram or the like. For example, an a.c. voltage usable is up to 20 V and a d.c. voltage usable is up to 50 V. It is preferable to use d.c. in order to heat the heater having the same resistance to a higher temperature. In the following description, it is assumed that d.c. drive current is flowed through the plane heater.

The control circuit 12 is constituted by a central processing unit CPU and receives detection signals from synthesized temperature sensors 9a and 9b, a target temperature signal entered by a key 16, an activation/iterception instruction signal from a key 19, and other signals.

The detection signals from the synthesized temperature detecting sensors 9a and 9b are converted into voltage signals by current/voltage converter circuits 13a and 13b and supplied to a selector circuit 21 in the control circuit 12. The selector circuit 21 periodically supplies two temperature signals to a conversion circuit 22. The conversion circuit 22 calculates measured temperatures T in accordance with the temperature detection signals to make a temperature display device 15 display an averaged detection temperature and supply the temperature detection signals to a control block 24.

The selector circuit 21 also supplies the detected temperature signals to an abnormal detector circuit 23. When the abnormal detector circuit 23 detects an abnormally high temperature, it immediately supplies an abnormal detection signal to a protector circuit 28. The protector circuit 28 controls the power supply source 11 to stop a power supply to the plane heaters 3a and 3b.

The abnormal detection signal is also supplied from the abnormal detector circuit 23 to the control block 24. The control block 24 stops the normal control while the abnormal state is detected.

Similarly, a knife use signal is supplied from an electric knife apparatus or laser knife apparatus 40 in the operation room to the abnormal detector circuit 23. Since large noises are generated while the knife is used, the abnormal detector circuit 23 generates an abnormal detection signal and stops driving the plane heaters, similar to when the abnormal high temperature is detected. As indicated by a broken line, the knife use signal may be supplied directly to the protection circuit 28.

The target temperature $T_0$ set with the key 16 is displayed on a setting temperature display device 17, and supplied to the control block 24.

As the heating operation is turned on by the key 19, the control block 24 compares the measured temperature T sent from the conversion circuit 22 with the target temperature To, and generates an instruction signal to a heater prediction control circuit 25 through predetermined calculation. The heater prediction control circuit 25 controls the power supply source 11 while predicting a change in the detected temperature.

Figure 7:
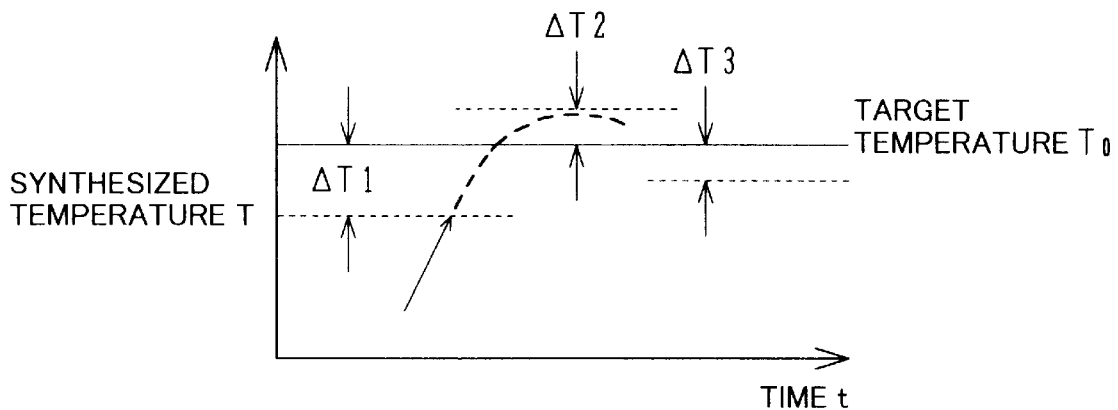
FIG. 7 is a graph illustrating synthesized temperature control for the air mat.

FIG. 7 is a graph briefly illustrating prediction control. The abscissa represents a time t and the ordinate represents a synthesized temperature T. The target temperature set with the key 16 is represented by $T_0$. As the synthesized temperature T gradually rises by heat generated by the plane heaters 3a and 3b and when the synthesized temperature T reaches a comparison temperature $T_0-\Delta T_1$, lower than the target temperature by $\Delta T_1$, the power supply to the plane heaters is stopped. At this time, for example, the plane heater is 70° C. which is higher than the synthesized temperature T of 38° C. Even if the drive current for the plane heaters is turned off, the synthesized temperature T continues to rise for some time. Therefore, the comparison temperature $T_0-\Delta T_1$, is set while taking this temperature rise overshoot into consideration. As the power supply to the plane heaters is stopped, the temperature rise gradually becomes gentle, the temperature saturates in the meantime, and thereafter it starts failing.

Even if the drive current is supplied again to the heater when the detected synthesized temperature T falls and reaches the target temperature $T_0$, the synthesized temperature T does not recover immediately. There is a time delay before the heat quantity generated by the heater influences the synthesized temperature. From this reason, when the temperature becomes lower than $T_0+\Delta T_2$ after the drive current supply to the plane heaters is stopped and after the temperature rise saturates, driving the plane heaters resumes. After driving the plane heaters resumes, the synthesized temperature lowers in the meantime and thereafter starts rising because of the influence of heat generation of the plane heaters. By predicting a change in the synthesized temperature in the above manner, the synthesized temperature T is controlled near at the target temperature $T_0$.

It is preferable that relatively large current is flowed at the initial temperature rise in order to raise the temperature to the setting temperature in a short time. In this case, since the overshoot of the synthesized temperature becomes large, the value $\Delta T_1$ is set larger.

After the synthesized temperature T reaches once near at the target temperature $T_0$, it is preferable to set the drive current for the plane heaters lower than the initial drive current in order to improve a precision of temperature control. In this case, a comparison temperature $T_0-\Delta T_3$ when the drive current supply resumes is preferably set higher than the initial comparison temperature $T_0-\Delta T_1$. If $\Delta T_2$ and $\Delta T_3$ can be set smaller, it is possible to control the synthesized temperature $T_0$ in a narrow temperature range. However, the same magnitude of the drive current may be used, and the same value for $\Delta T_1$ and $\Delta T_3$ may be used.

Figure 8:
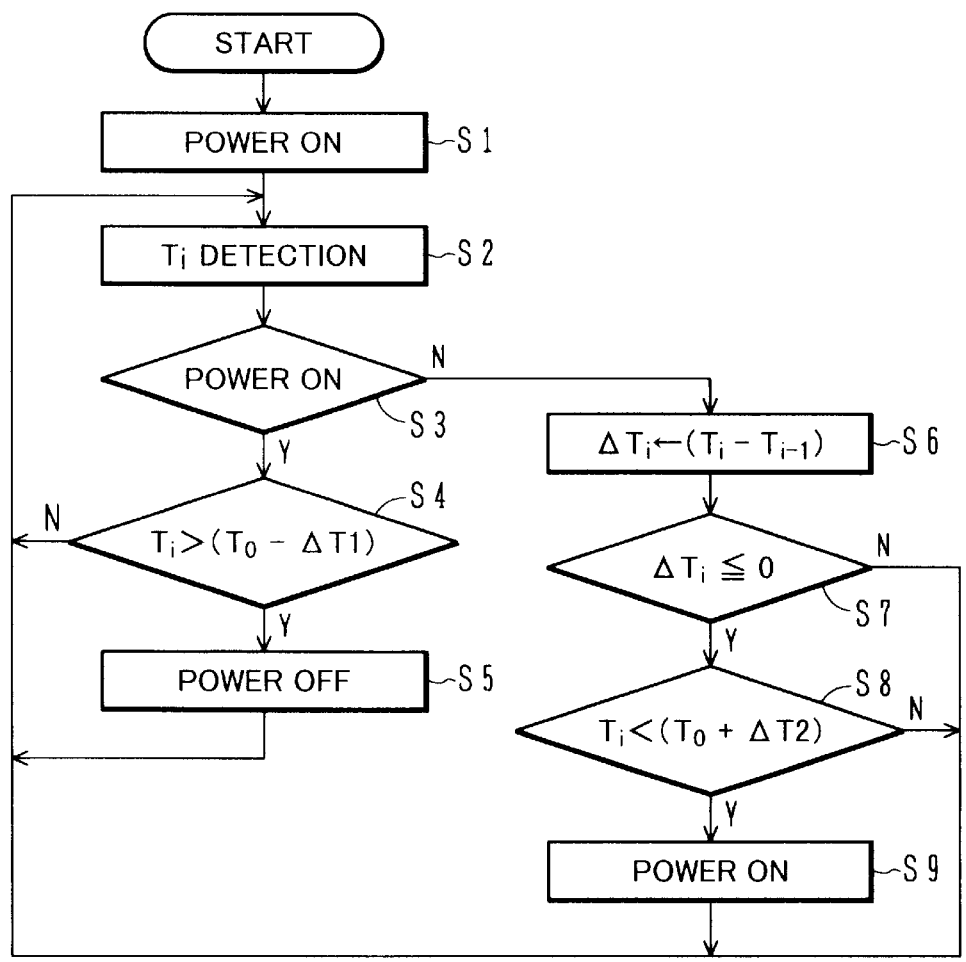
FIG. 8 is a flow chart illustrating an example of synthesized temperature control for the air mat.

FIG. 8 is a flow chart illustrating temperature control with the same magnitude of the drive current. As the control starts, power is turned on at step S1 to heat the plane heaters 3a and 3b. Next, at step S2, the synthesized temperature T is measured. This measurement is periodically performed and the detected temperature T at a certain time is represented by $T_i$.

A plurality of measurement results may be averaged to obtain $T_i$. If a plurality of synthesized temperature detecting sensors are used, a higher synthesized temperature or an average value is used.

Next, at step S3 it is checked whether the power is being turned on. If on, the flow follows an arrow with Y and advances to step S4 whereat it is checked whether the detected temperature $T_1$ is higher than the comparison temperature $(T_0-\Delta T_1)$. This judgement is negated until the synthesized temperature T reaches the comparison temperature $(T_0-\Delta T_1)$ so that the flow follows an arrow with N and returns to step S2.

When the detected temperature $T_i$ becomes higher than the comparison temperature $(T_0-\Delta T_1)$, the flow follows an arrow with Y and advances to step S5 whereat the drive current for the plane heaters is turned off. After the drive current for the plane heaters is turned off, the flow returns again to step S2 to detect the synthesized temperature. The synthesized temperature continues to rise in the meantime because of remaining heat.

The judgement at step S3 under a power turn-off state is negated so that the flow follows an arrow with N arid advances to step S6 whereat a difference $(T_i-T_{i-1})$ between the present detected temperature $T_i$ and the previous detected temperature $T_{i-1}$ is calculated, this difference being represented by $\Delta T_i$.

Next, at step S7 it is judged whether $\Delta T_i$ is 0 or negative. When $\Delta T_i$ becomes 0 or negative means that the temperature rise ends and the temperature falls thereafter. Therefore, the flow follows an arrow with Y and advances to step S8.

At step S8 it is checked whether the detected temperature $T_i$ is lower than the comparison temperature $(T_0+\Delta T_2)$. If the detected temperature $T_i$ is lower than the comparison temperature $(T_0+\Delta T_2)$, it means that the synthesized temperature will soon become lower than the target temperature $T_0$. Therefore, the flow follows an arrow with Y and advances to step S9 whereat the power to the plane heaters is turned on. Thereafter, the flow returns again to step S2.

If the temperature change $\Delta T_i$, at step S7 is positive after the power is turned off, the temperature rise still continues so that the flow follows an arrow with N and returns back to step S2. Similarly, if the detected temperature $T_i$ is higher than the comparison temperature $(T_0+\Delta T_2)$ at step S8 although the temperature rise ended, the flow follows the arrow with N and returns to step S2 because if the drive current is again supplied, the temperature becomes higher than the target temperature.

In the above manner, the temperature control with a small overshoot becomes possible by predicting a change in the synthesized temperature by using the set temperature change prediction widths $\Delta T_1$ and $\Delta T_2$ on both sides of the target temperature $T_0$.

Figure 9:
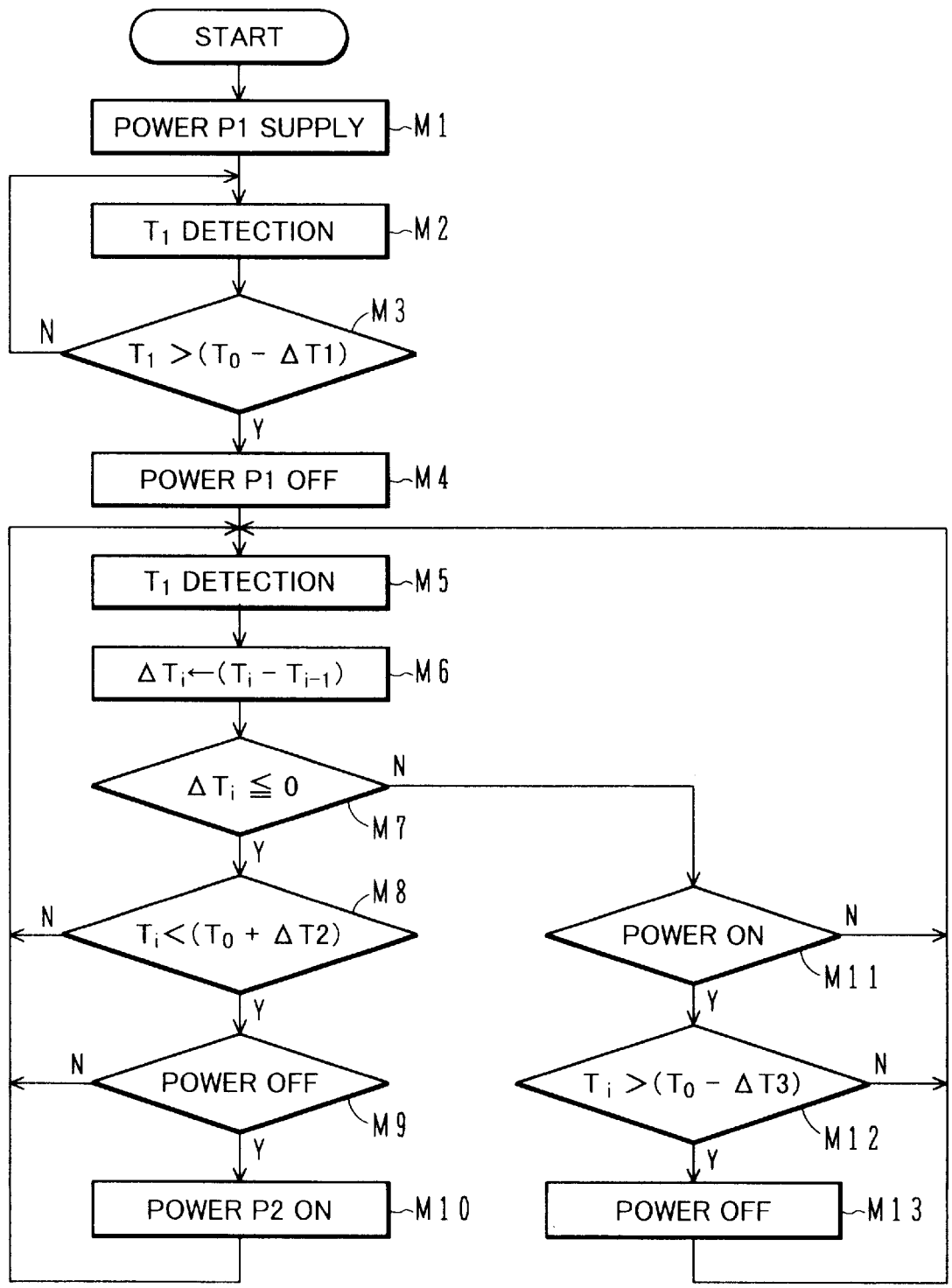
FIG. 9 is a flow chart illustrating another example of synthesized temperature control for the air mat.

FIG. 9 shows another example of temperature control with higher precision. As the control starts, power P1 is supplied at step M1 to start heating the plane heaters. This power P1 is set to a large value so that the air mat is heated to a predetermined temperature in a short time.

Next, at step M2 the temperature $T_i$ is detected. At step M3 it is checked whether the temperature $T_i$ is higher than the comparison temperature $(T_0-\Delta T_1)$. If the temperature $T_i$ is not higher than the comparison temperature $(T_0-\Delta T_1)$, it is judged that heating is still necessary, and the flow follows an arrow with N and returns to step M2.

When the detected temperature $T_i$ becomes higher than the comparison temperature $(T_0-\Delta T_1)$, it is judged that heating sufficient for reaching the target temperature To has been made, and the flow follows an arrow with Y and advances to step M4 whereat the power P1 is turned off.

After the power is turned off, at step M5 the synthesized temperature $T_i$ is again detected periodically. At step M6 a difference $(T_i-\Delta T_{i-1})$ between the present detected temperature $T_i$ and the previous detected temperature $T_{i-1}$ is obtained, this difference being represented by $\Delta T_i$.

Next, at step M7 it is judged whether $\Delta T_i$ is 0 or negative. When $\Delta T_i$ becomes 0 or negative means that the synthesized temperature falls thereafter.

If $\Delta T_i$ becomes 0 or negative, the flow follows an arrow with Y and advances to step M8 whereat it is checked whether the detected temperature $T_i$ is lower than the comparison temperature $(T_0+\Delta T_2)$. If the detected temperature $T_i$ is lower than the comparison temperature $(T_0+\Delta T_2)$, the flow follows an arrow with Y and advances to step M9 whereat it is judged whether the power is being turned off. if the power is being turned off, the flow follows an arrow with Y and advances to step M10 whereat a power P2 is turned on and thereafter the flow returns to step M5. Heating the plane heaters resumes not to make the synthesized temperature too low. The power P2 is selected smaller than P1 so as to make it suitable for heat insulation.

If the detected temperature $T_i$ is not Lower than the comparison temperature $(T_0+\Delta T_2)$ at step M8, it is not necessary to resume heating so that the flow follows an arrow with N and returns to step M5. If the power is not turned off at step M9, the flow follows the arrow with N to return to step M5 because the power has already been turned on.

If the temperature change $\Delta T_i$ is positive at step M7, the flow follows an arrow with N and advances to step M11 whereat it is checked whether the power is turned on. If the power is turned on, it means that the power P2 was turned on at step M10. In this case, the flow follows an arrow with Y and advances to step M12.

At step M12 it is checked whether the detected temperature $T_i$ is higher than the comparison temperature $(T_0-\Delta T_3)$. If the detected temperature $T_i$ is higher than the comparison temperature $(T_0-\Delta T_3)$, it is judged that heating sufficient for reaching the target temperature $T_0$ has been made, and the flow follows an arrow with Y and advances to step M13 whereat the power is turned off. Thereafter, the flow returns to step M5.

If the power is not supplied at step M11, this state means that the temperature rise still continues although the power was turned off. Therefore, the flow follows an arrow with N and returns to step M5. If the detected temperature $T_i$ is not higher than the comparison temperature $(T_0-\Delta T_3)$ at step M12, it means that heating is required to continue in order to reach the target temperature $T_0$, and the flow follows an arrow with N and returns to step M5.

In the control illustrated in FIG. 9, the comparison temperature $(T_0-\Delta T_1)$ at the initial heating and the comparison temperature $(T_0-\Delta T_3)$ at the second heating can be set independently. The drive power P1 for initial heating and the drive power P2 for second heating can also be set independently. Therefore, the control more finer than that illustrated in FIG. 8 is possible.

Figure 10A:
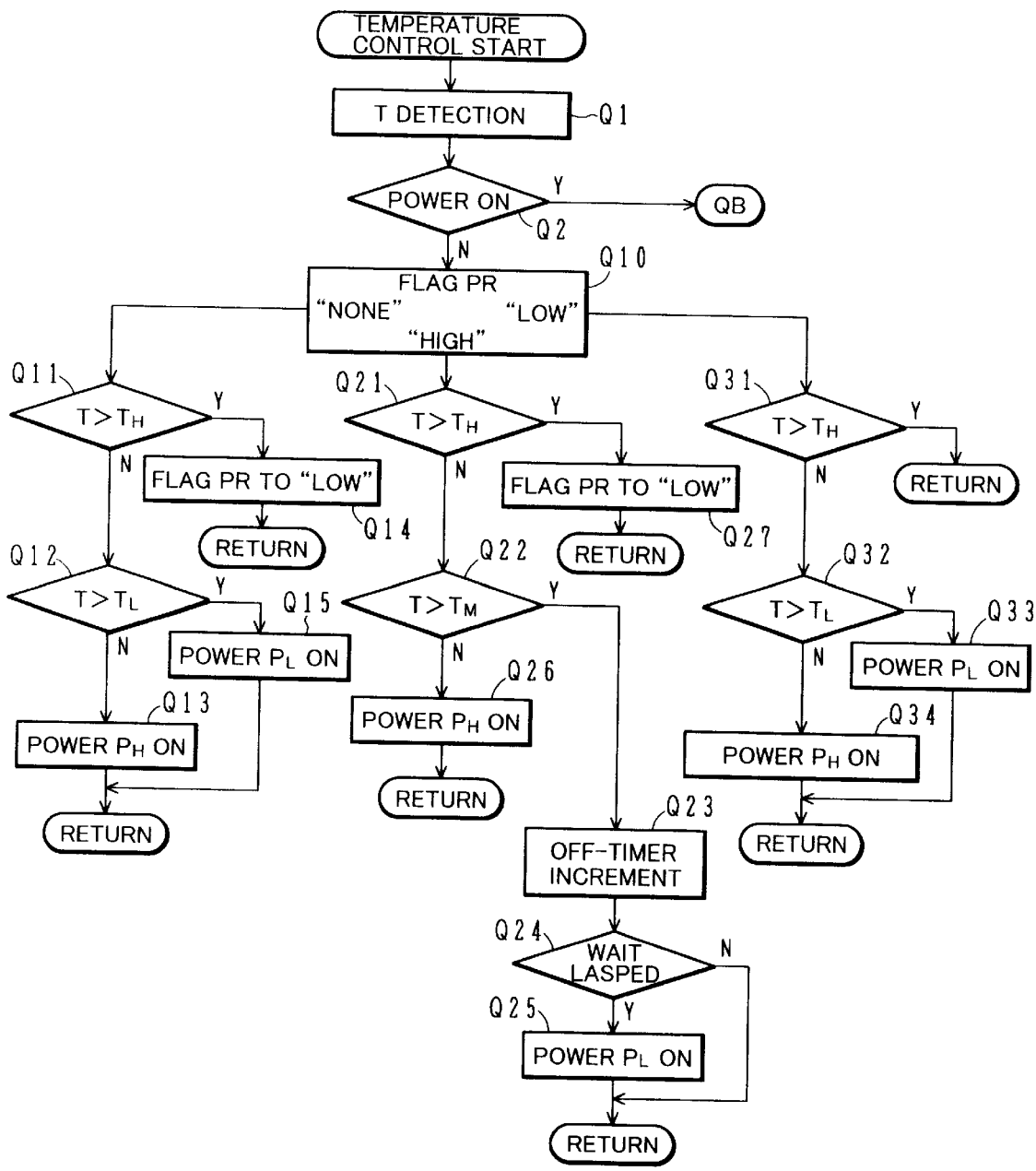
FIGS. 10A and 10B are flow charts illustrating another example of synthesized temperature control for the air mat.
Figure 10B:
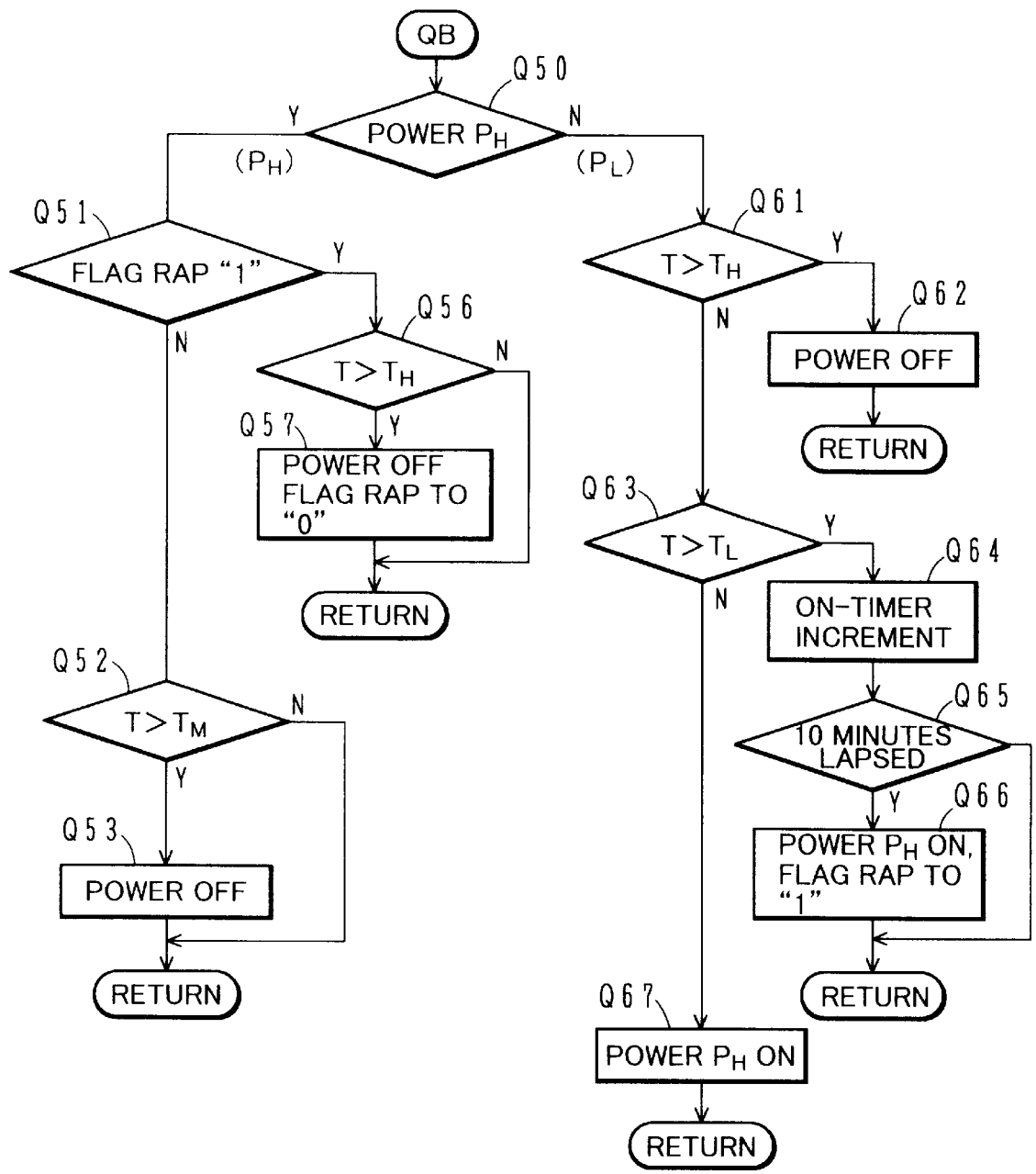

FIGS. 10A and 10B are flow charts showing another example of synthesized temperature control.

This control process is repeated at a constant timing. In this control, three comparison temperatures lower than the target temperature as well as two drive powers are used. Thermal history is judged from whether the present power is on or off, and if the power is off, from whether the previous power supply was high power or low power.

As the comparison temperatures, for examples, temperatures lower than the target temperature by 0.5° C., 5° C., and 8° C. are used. If the present synthesized temperature is lower than the target temperature by 8° C. or more, heating is performed with a large power.

In FIG. 10A, as the process starts, the synthesized temperature T is detected at step Q1. Next, at step Q2 it is judged whether power is presently supplied. If the power is supplied, it means that the heaters are being heated, and the flow follows an arrow with Y and moves to the process after terminal QB shown in FIG. 10B.

At the start-up, power is not still supplied so that the judgement at step Q2 is negated and the flow follows an arrow with N and advances to step Q10.

At step Q10, the flow is branched in accordance with a flag PR indicating the previous power supply state. At the start-up, the flag PR is "none". If the previous power supply is high power, the flag PR is basically "high", and if low power, the flag PR is "low".

If the flag PR is "none" at the start-up, the flow advances to step Q11 whereat it is checked whether the detected synthesized temperature T is higher than a higher comparison temperature $T_H$. Generally, the synthesized temperature T is much lower than the high comparison temperature $T_H$ and the flow follows an arrow with N and advances to step Q12.

At step Q12 it is checked whether the synthesized temperature T is higher than a low comparison temperature $T_L$. If the synthesized temperature T is not higher than the low comparison temperature $T_L$, the flow advances to step Q13 whereat a high power $P_H$ is supplied to heat the bed at a fast heating speed. Although large heating with the high power can raise the temperature of the bed in a short time, it is not suitable for temperature control with high precision. Near at the target temperature, small heating with a low power enables temperature control with higher precision.

In summer or the like, the synthesized temperature T is higher than the low comparison temperature $T_L$ in some cases. In such cases, the judgement at step Q12 is Yes and the flow advances to step Q15 whereat a low power $P_1$ is supplied. In this case, the bed raises its temperature at a relatively slow speed. When the high power $P_H$ and low power $P_L$ are supplied, the flag PR is set to "high" and "low", respectively.

If the synthesized temperature T is already higher than the high comparison temperature $T_H$ at step Q11, it is not necessary to heat the bed, and the flow follows an arrow with Y and advances to step Q14 whereat the flag PR is set to "low".

At the start-up, generally the high power $P_H$ is supplied to the heaters at step Q13 or the low power $P_L$ is supplied to the heaters at step Q15. After the process returns, since the power is being supplied at step Q2, the flow follows the arrow with Y and advances to step Q50 shown in FIG. 10B.

At step Q50 it is checked whether the supplied power is the high power $P_H$. If the high power, the flow follows an arrow with Y and advances to step Q51.

At step Q51 it is checked whether a flag RAP is "1". The flag RAP is normally "0" and so the flow follows an arrow with N and advances to step Q52.

At step Q52 it is checked whether the synthesized temperature T is higher than a middle comparison temperature $T_M$. If the synthesized temperature T becomes higher than the middle comparison temperature $T_M$ because of heating by the heaters, the flow follows an arrow with Y and advances to step Q53 whereat the supplied power is turned off. Thereafter, the process returns. If the synthesized temperature T is not higher than the middle comparison temperature $T_M$, the flow bypasses step Q53 to continue the power supply.

In the above manner, if the high power $P_H$ is supplied at the start-up, this power supply continues until the synthesized temperature T becomes higher than the middle comparison temperature $T_M$, and when it exceeds the middle comparison temperature $T_M$, the power supply is stopped. Even if the power supply is stopped, the bed continues to raise its temperature because of remaining heat.

If the power is turned off at step Q53, the judgement at the next step Q2 is negated and the flow follows the arrow with N and advances to step Q10.

As described above, if the previous power supply is the high power, the flag PR is "high" and the flow advances to step Q21.

At step Q21 it is checked whether the synthesized temperature T becomes higher than the high comparison temperature $T_H$. The synthesized temperature generally reaches the high comparison temperature $T_H$ immediately because the high power supply is stopped at the middle comparison temperature $T_M$.

If the synthesized temperature r is not higher than the high comparison temperature $T_H$, the flow follows an arrow with N and advances to step Q22 whereat it is checked whether the synthesized temperature T is higher than the middle comparison temperature $T_M$.

Since the high power was supplied until the synthesized temperature T exceeds the middle comparison temperature $T_M$, the judgement at step Q22 is generally Yes and the flow follows an arrow with Y and advances to step Q23.

At step Q23, an off-timer is incremented, the off-timer counting a time length of the power supply stop period after the high power supply is stopped. Next, at step Q24 it is checked whether the count of the off-timer exceeds a count preset for a wait time.

If the synthesized temperature T does not reach the high comparison temperature $T_H$ and the wait time has lapsed, the Low power $P_L$ starts being supplied. Thereafter, the process returns. The process at step Q24 is No until the count of the off-timer reaches the wait time, and the flow follows an arrow with N to bypass step Q25.

Specifically, if the synthesized temperature T does not reach the high comparison temperature $T_H$ in a predetermined wait period (e.g., 3 minutes) after the high power is supplied, the power is again supplied. If the synthesized temperature is higher than the middle comparison temperature $T_M$ even after the wait period is lapsed, the low power $P_L$ is supplied.

If the synthesized temperature T becomes equal to or lower than the middle comparison temperature $T_M$ before the lapse of the wait time, the judgement at step Q22 is No. This means that heat consumption is larger than remaining heat or other cases. In such a case, the flow follows an arrow with N and advances to step Q26 whereat the high power $P_H$ is supplied. In this case, the control same as described above is repeated.

If the synthesized temperature T becomes higher than the high comparison temperature $T_H$ within the wait time, the flow follows an arrow with Y from step Q21 and advances to step Q27. Since sufficient temperature rise was obtained, the flag PR is changed to "low".

As the lower power $P_L$ starts being supplied at step Q25 after the initial heating, the judgement at the step Q50 shown in FIG. 10B is No, and the flow follows an arrow with N and advances to step Q61.

Until the synthesized temperature T reaches the high comparison temperature $T_H$, the flow follows an arrow with N and advances to step S63 whereat it is checked whether the synthesized temperature T is higher the low comparison temperature $T_L$. If the synthesized temperature T is higher the low comparison temperature $T_L$, the flow advances to step Q64 whereat an on-timer is incremented, the on-timer counting a time length of the low power supply period.

Next, at step Q65 it is checked whether the time of the on-timer has lapsed, for example, 10 minutes. The process returns until 10 minutes lapse. If the synthesized temperature T becomes higher than the high comparison temperature $T_H$ within 10 minutes, the flow follows an arrow with Y from step Q61 and advances to step Q62 whereat the power supply is stopped.

If the synthesized temperature does not exceed $T_H$ after the lapse of 10 minutes, the flow follows an arrow with Y from step Q65 and advances to step Q66 whereat the high power $P_H$ is supplied and the flag RAP is set to "1". Thereafter, the process returns.

In this case, the judgement at the next step Q50 is Yes and that at the next step Q51 is Yes. At step Q56 it is checked whether the synthesized temperature T exceeds the high comparison temperature $T_H$, and if exceeds, the flow advances to step Q57 whereat the power is turned off and the Flag RAP is reset to "0".

Specifically, if the synthesized temperature does not reach the high comparison temperature $T_H$ regardless of the supply of the low power for 10 minutes, it is judged that fast heating is necessary and the high power is supplied. For the discrimination between these states, the flag RAP is set.

If the synthesized temperature r becomes higher than the low comparison temperature $T_L$ before the lapse of 10 minutes, it is judged that the synthesized temperature lowered too much. The flow advances from Step Q63 to step Q67 whereat the high power $P_H$ is supplied.

Although the low power supply period is set to 10 minutes, it may be changed with available power, the conditions of an operation room, and the like.

If the synthesized temperature exceeds the high comparison temperature $T_H$ by the low p power supply, the flow advances from step Q61 to step Q62 whereat the power supply is stopped. After this, the judgement at step Q10 is "low" and the flow advances to step Q31.

At step Q31 it is checked whether the synthesized temperature T is higher than the high comparison temperature $T_H$. If the synthesized temperature T is higher than the high comparison temperature $T_H$, the flow follows an arrow with Y and directly returns.

If the synthesized temperature T is not higher than the high comparison temperature $T_H$, the flow follows an arrow with N and advances to step Q32 whereat it is checked whether the synthesized temperature T is higher than the low comparison temperature $T_L$. If the synthesized temperature T is higher than the low comparison temperature $T_L$, the flow follows an arrow with Y and advances to step Q33 whereat the low power $P_L$ is supplied. Namely, if the synthesized temperature T exceeds the high comparison temperature $T_H$, the low power $P_L$ is turned off, and if lowers below $T_H$, the low power $P_L$ is turned on.

The case wherein the synthesized temperature T is higher than the low comparison temperature $T_L$ at step Q32 does not usually occur. If it happens, the flow advances to step Q34 to supply the high power $P_H$. Steps Q34 and Q67 are used for rapidly heating with high power if the synthesized temperature lowers quickly because of specific causes which do not occur in an ordinary case.

In the control flow shown in FIGS. 10A and 10B, the prediction control is executed in accordance with the past power supply, without detecting the temperature change ΔT. The middle comparison temperature $T_M$ is used only for stopping the high power supply and for monitoring the succeeding state, and is set lower than the high comparison temperature $T_H$. This middle comparison temperature $T_M$ is not necessarily required to be higher than the low comparison temperature $T_L$. Two comparison temperatures may be used by setting $T_M$ and $T_L$ equal.

In the above control, if two types of powers are used, these powers are generated from full waves or half waves of an a.c. power. If a d.c. drive is utilized. Full waves or half waves may be formed by a triac and then rectified. The power can be generated with a simple structure.

In the control illustrated in FIGS. 8, 9, 10A, and 10B, only the control portion using the synthesized temperature T is shown. If an abnormal signal is detected from the plane heater temperature detecting sensor or from an electric knife, the control is intercepted irrespective of the above control flow.

Figure 11A:
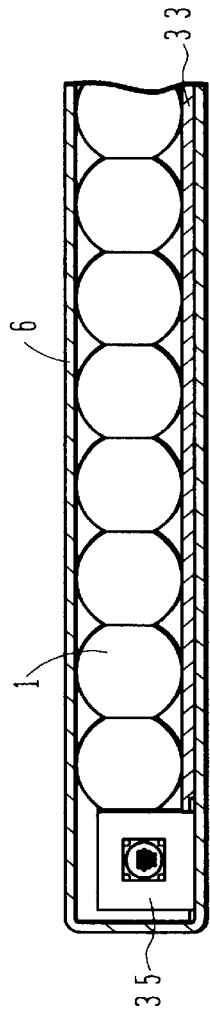
FIG. 11A is a cross sectional view of an air mat according to another embodiment of the invention.

FIG. 11A shows an air mat with a heating function according to another embodiment of the invention. A plurality of air cells 1 are juxtaposed and the side wall of adjacent cells are bonded together through welding or the like. A support sheet 33 accommodating plane heaters therein is disposed under the air cells 1.

A bag 6 is disposed covering the air cells and support sheet 33. At the si de of the juxtaposed air cells 1, a connector 35 for compressed air and power is disposed.

Figure 11B:
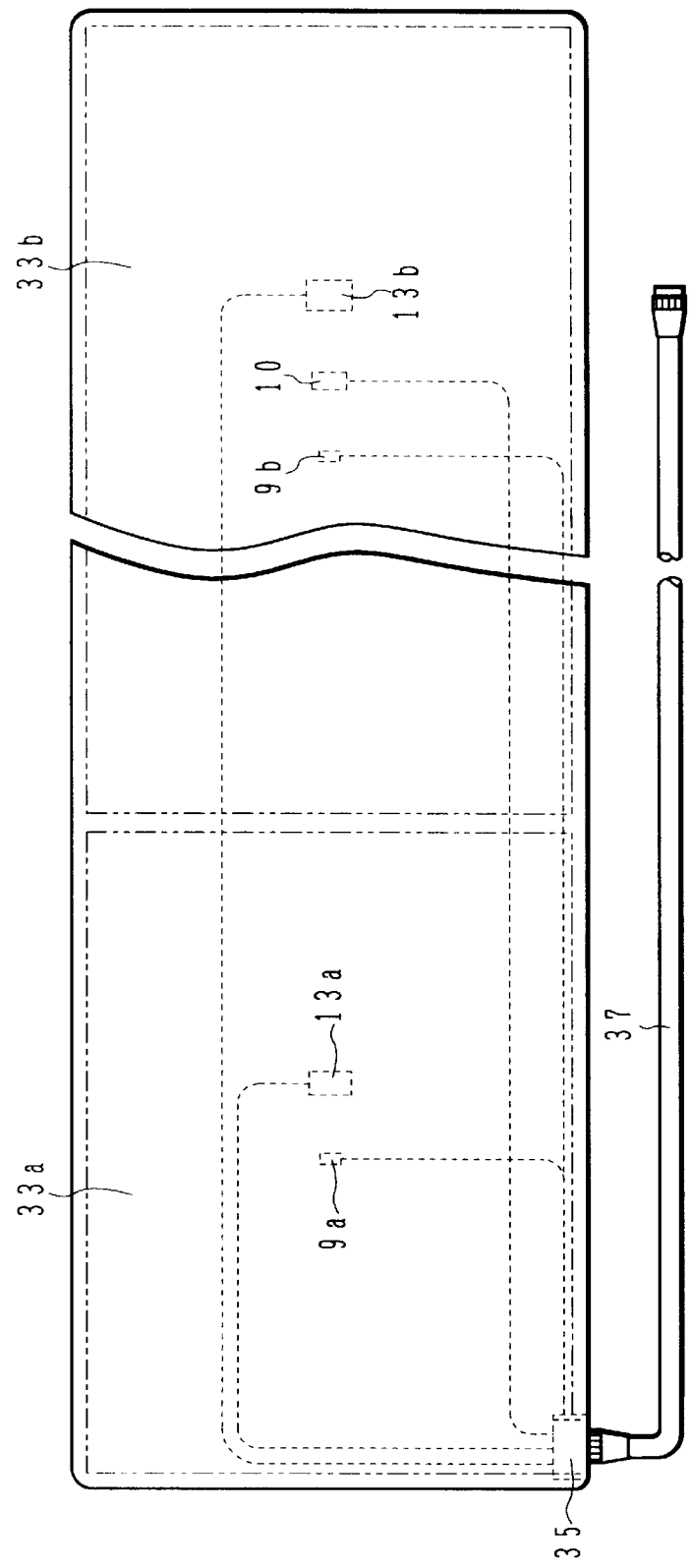
FIG. 11B is a plan view of the air mat shown in FIG. 11A.

FIG. 11B is a plan view of the air mat shown in FIG. 11A. The plane heaters are two divided plane heaters 33a and 33b. The plane heater 33b corresponds to an upper body of a patient, and the plane heaters 33a and 33b correspond to the whole body of the patient.

On the plane heaters 33a and 33b, temperature fuses 13a and 13b are disposed. On the upper surface of the air mat, synthesized temperature detecting sensors 9a and 9b are disposed for the plane heaters 33a and 33b. A thermistor 10 for detecting the e heater temperature is provided only for the plane heater 33b for the upper body. A coupling tube 37 is connected to the socket 35 in order to transfer compressed air, drive current, and detection signals.

Figure 12A:
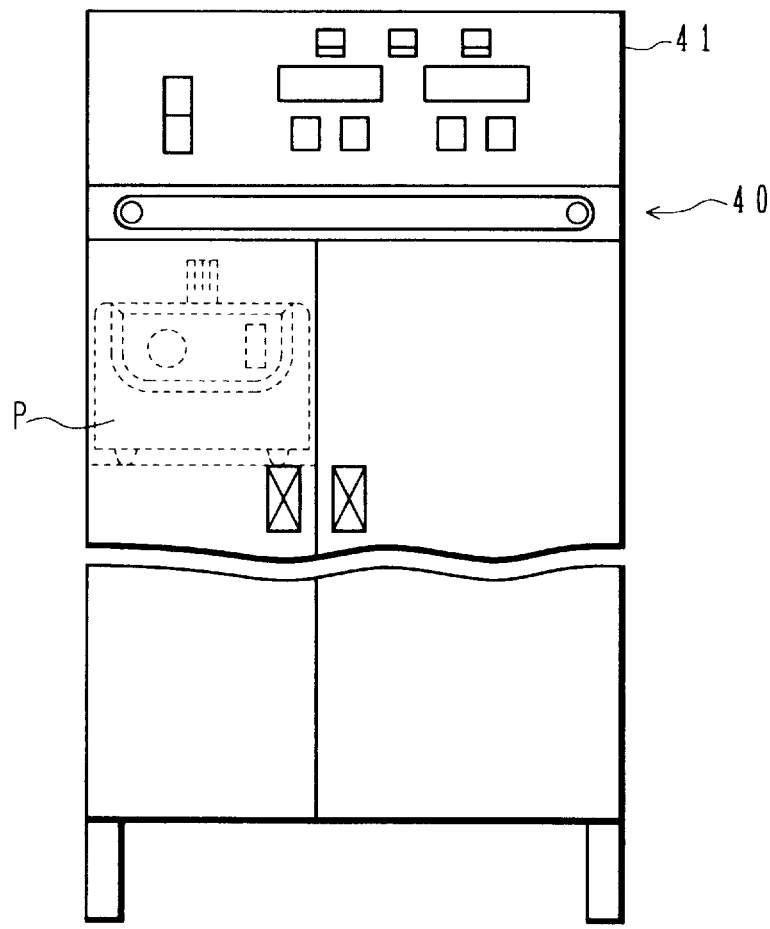
FIGS. 12A to 12C are a plan view, a partial front view, and a rear view of a heater control apparatus of an air mat.
Figure 12B:
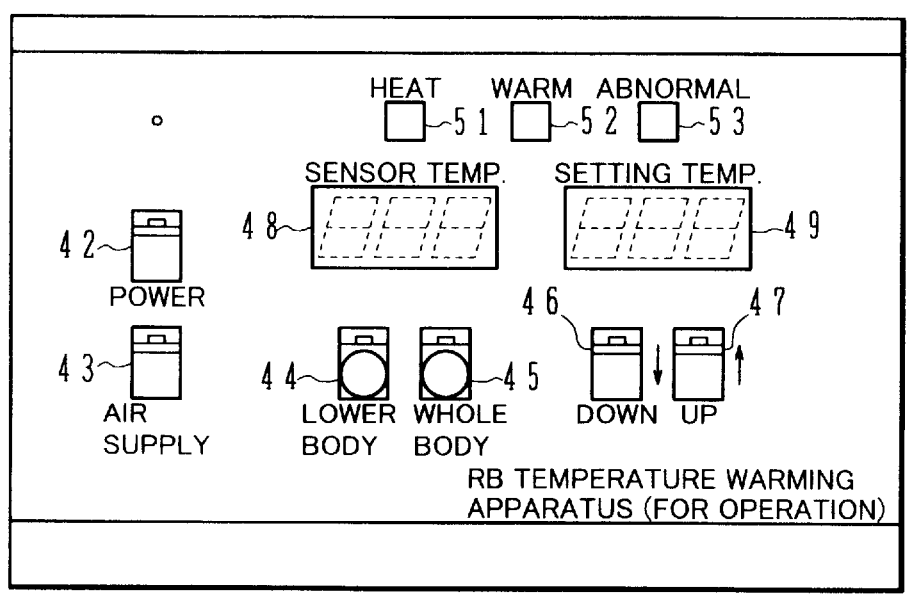
Figure 12C:
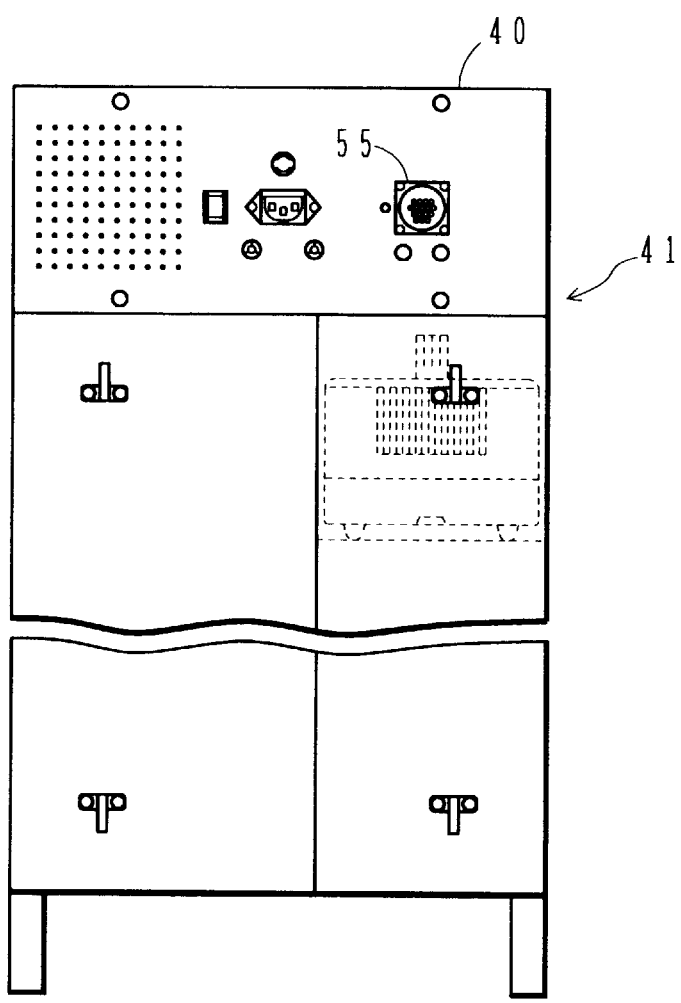

The coupling tube is connected to a control apparatus shown in FIGS. 12A to 12C. In FIG. 12A, the upper front of the control apparatus 40 is mounted with a control panel 41 under which an air pump P is mounted.

As shown in FIG. 12B, t he control panel 41 has therein a power switch 42, an air supply switch 43, an upper body heating switch 44, a whole body heating switch 45, a setting temperature lowering switch 46, and a setting temperature raising switch 47. The synthesized temperature is displayed on a display device 48, and the setting temperature is displayed on a display device 49. Lamps 51, 52, and 53 are disposed above these display devices 48 arid 49, for displaying a heating state, a temperature maintaining state, and an abnormal state, respectively.

As shown in FIG. 12, at the back of the control apparatus, a socket 55 is disposed which is connected to the coupling tube 37 shown in FIG. 11B. The control apparatus is accommodated in a metal housing. The power sources for the heaters and control circuit are made of electrically shielded transformers and the like and are accommodated in the metal housing. Electrical shield prevents a cardiogram or the like from being adversely affected.

Figure 13:
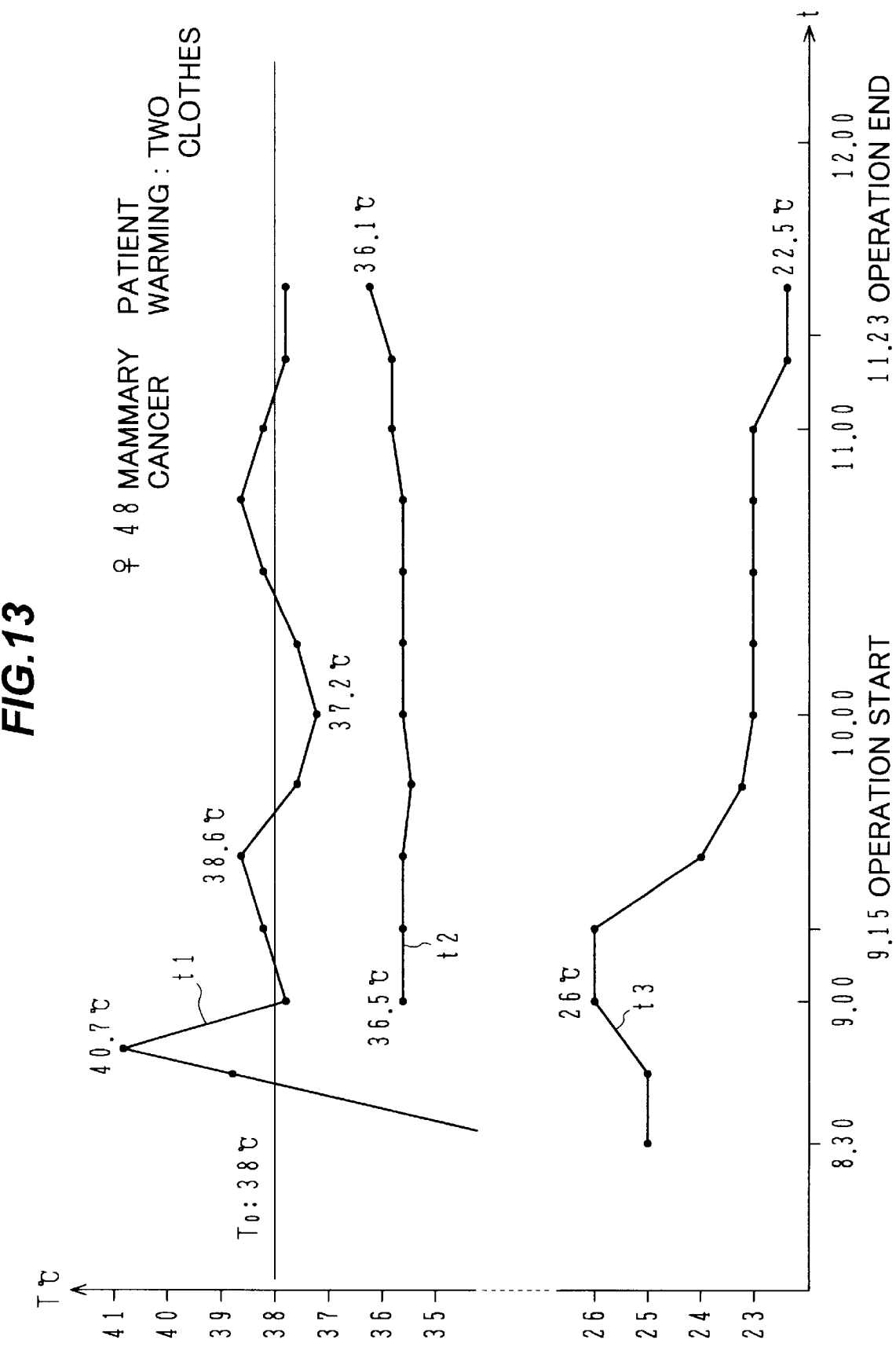
FIG. 13 is a graph showing a bodily temperature holding performance of the air mat according to the embodiment of the invention.

FIG. 13 is a graph showing the measurement results of the air mat for an operation bed described above. The abscissa represents a time lapse t and the ordinate represents a synthesized temperature T. The setting temperature is 38° C.

A curve t1 indicates the synthesized temperature detected with the synthesized temperature detecting sensor during the control illustrated in FIGS.10A and 10B under the conditions of $T_M=T_L=T_0-5°$ C. and $T_H=T_0-0.5°$ C. At the initial heating, the synthesized temperature t1 rises once to 40.7° C., thereafter lowers, and is maintained about the setting temperature 38° C.

In the state shown in FIG. 13, the synthiesized temperature is maintained in the range from 37.2° C. to 38.6° C. excepting the initial overshoot.

A curve t2 indicates a change in the temperature of the patient. The patient temperature is maintained generally constant although it lowers slightly after the operation start, and is 36.1° C. at the wake-up after the operation end. For comparison, the temperature t3 of the operation room is shown below the curves t1 and t2. The room temperature t3 is lowered after the operation starts, maintained about 23° C. during the operation, and lowers to 22.5° C. after the operation. Therefore, even if the room temperature is cooled to about 23° C., the patient temperature can be maintained about 36° C.

The above measurements are obtained by setting two types of comparison temperatures for temperature rise. If three types of comparison temperatures are set as in the control illustrated in FIGS. 10A and 10B, finer control is possible. For example, the initial overshoot can be reduced further.

In the above description, the plane heater drive current is turned on and off or changed among large, small, and off. If the air mat is in use, the drive current may not be turned off, but the current off-state may be replaced by an idle state wherein a small current is flowed constantly. The current value may be set to multi-level. Furthermore, the current value may be controlled successively.

The present invention has been described in connection with the preferred embodiments. The invention is not, limited only to the above embodiments. It is apparent to those skilled in the art that various modifications, improvements, combinations and the like can be made without departing from the scope of the appended claims.

I claim:

1. A method of controlling the temperature of an air mat for an operation bed capable of periodically changing a support area of a patient, comprising the steps of:

activating a heater for providing heat wherein the heater is on a lower surface of an air layer of the air mat;

measuring a synthesized temperature with a sensor provided on an upper surface of the air layer of the air mat and in a region on which the patient lies, the synthesized temperature being a composite temperature of both the patient and the air layer;

comparing the synthesized temperature with a first comparison temperature lower than a target temperature by a first predetermined temperature differential; and reducing drive current to the heater when the measured temperature reaches the comparison temperature.

2. A method of controlling the temperature of an air mat for an operation bed according to claim 1, further comprising the steps of:

obtaining a remainder of the synthesized temperature subtracted from a previous measured temperature; and controlling the heater in accordance with the synthesized temperature and the remainder.

3. A method of controlling the temperature of an air mat for an operation bed according to claim 2, wherein said controlling step includes a temperature maintaining step of increasing the drive current of the heater when said remainder becomes 0 or negative and the synthesized temperature becomes lower than a second comparison temperature higher than the target temperature by a second predetermined temperature differential.

4. A method of controlling the temperature of an air mat for an operation bed according to claim 3, wherein said controlling step includes a temperature rise preventing step of reducing the drive current of the heater when said remainder becomes positive and the synthesized temperature becomes higher than a comparison temperature lower than the target temperature by a third predetermined temperature differential.

5. A method of controlling the temperature of an air mat for an operation bed according to claim 3, wherein said activating and heating step and said temperature maintaining step of said control step are performed at different current values.

6. A method of controlling the temperature of an air mat for an operation bed according to claim 1, further comprising the controlling step of controlling a current supply in accordance with the synthesized temperature and a history of the current supply.

7. A method of controlling the temperature of an air mat for an operation bed according to claim 6, wherein said controlling step performs different controls for a case where the synthesized temperature has once exceeded another comparison temperature higher than said comparison temperature and for another case where the synthesized temperature has not exceeded said another comparison temperature.

8. A method of controlling the temperature of an air mat for an operation bed according to claim 7, wherein the step of reducing the drive current comprises the step of turning off the drive current and further includes the step of measuring time length of current turn-off.

9. A method of controlling the temperature of an air mat for an operation bed according to claim 8, wherein said controlling step supplies a drive current smaller than said drive current when the synthesized temperature does not exhibit a predetermined temperature rise even when the time length of current turn-off reaches a set value.

10. A method of controlling the temperature of an air mat for an operation bed according to claim 1, wherein said target temperature is in a range from 35° C. to 39° C.

11. A method of controlling the temperature of an air mat for an operation bed according to claim 1, wherein said air mat comprises first and second groups of air cells, further comprising the steps of:

supplying compressed air to said first group of air cells;

supplying compressed air to said second group of air cells while said first group of air cells are still in a pressured state; and releasing air pressure in said first group of air cells after said second group of air cells are sufficiently pressured.

12. A method of controlling the temperature of an air mat for an operation bed according to claim 1, further comprising the step of displaying said target temperature and said synthesized temperature.

* * * * *